(12) United States Patent
Navab

(10) Patent No.: US 6,731,283 B1
(45) Date of Patent: May 4, 2004

(54) C-ARM CALIBRATION METHOD UTILIZING APLANAR TRANSFORMATION FOR 3D RECONSTRUCTION IN AN IMAGING SYSTEM

(75) Inventor: Nassir Navab, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 09/001,772

(22) Filed: Dec. 31, 1997

(51) Int. Cl.⁷ .............................................. G06F 15/00
(52) U.S. Cl. ...................................................... 345/424
(58) Field of Search ................................ 345/419, 420, 345/421, 422, 423, 424

(56) References Cited

U.S. PATENT DOCUMENTS

| | | | |
|---|---|---|---|
| 4,618,978 A | 10/1986 | Cosman | 378/20 |
| 5,038,371 A | 8/1991 | Janssen et al. | 378/197 |
| 5,442,674 A | 8/1995 | Picard et al. | 378/20 |
| 5,524,187 A | * 6/1996 | Feiner et al. | 345/419 |
| 5,602,564 A | * 2/1997 | Iwamura et al. | 345/419 |
| 5,687,259 A | * 11/1997 | Linford | 345/435 |
| 5,706,324 A | 1/1998 | Wiesent et al. | 378/4 |
| 5,764,719 A | 6/1998 | Noettling | 378/4 |
| 5,852,646 A | 12/1998 | Klotz et al. | 378/8 |
| 5,864,146 A | 1/1999 | Karellas | 250/581 |

* cited by examiner

Primary Examiner—Phu K. Nguyen

(57) ABSTRACT

A C-arm calibration method for 3D reconstruction in an imaging system comprising an imaging source and an imaging plane, the method utilizing a planar transformation for relating voxels in a voxel space and pixels in the imaging plane, and comprises the steps of: defining a source coordinate system in reference to the imaging source; defining a normal plane in the voxel space, not including the origin of the source coordinate system and being substantially normal to an optical axis from the source to the imaging plane; defining a relationship between the source coordinate system and another coordinate system, herein referred to as a world coordinate system, by transformation parameters; identifying pixel location coordinates for a respective pixel corresponding to each voxel by utilizing planar to planar transformation parameters; storing a value of a filtered image at the respective pixel location; accumulating contributions corresponding to a plurality of image projections so as to thereby reconstruct each voxel; dividing the voxel space into a plurality of planes parallel to the normal plane; back projecting an image of a plurality of pixels on the image plane onto a set of coplanar voxels defining one of the plurality of parallel planes; defining a relationship in the source coordinate system between each of the plurality of pixels and corresponding ones of the coplanar voxels so as to obtain a 2-dimensional mapping between points on the one of the plurality of planes and pixels on the image plane.

9 Claims, 11 Drawing Sheets

C-ARM CALIBRATION METHOD UTILIZING APLANAR TRANSFORMATION FOR 3D RECONSTRUCTION IN AN IMAGING SYSTEM

The present invention relates to radiography imaging and, more specifically, to a C-arm calibration method and apparatus for 3D reconstruction using 2D planar transformations for back-projection.

The following patent applications in the name of the present inventor and whereof the disclosure is hereby incorporated by reference to the extent it is not inconsistent with the present invention, are being filed on even date herewith and are subject to obligation of assignment to the same assignee as is the present application.

A C-ARM CALIBRATION METHOD FOR 3D RECONSTRUCTION;
APPARATUS FOR C-ARM CALIBRATION FOR 3D RECONSTRUCTION IN AN IMAGING SYSTEM;
APPARATUS FOR C-ARM CALIBRATION FOR 3D RECONSTRUCTION IN AN IMAGING SYSTEM UTILIZING A PLANAR TRANSFORMATION;
APPARATUS FOR PROVIDING MARKERS ON AN IMAGE, FOR USE IN CONJUNCTION WITH C-ARM CALIBRATION APPARATUS; and
A C-ARM CALIBRATION METHOD FOR 3D RECONSTRUCTION IN AN IMAGING SYSTEM.

Recent years have seen an increasing interest in tomographic reconstruction techniques using two dimensional detectors. These techniques are better known as cone-beam reconstruction techniques.

Helpful background information can be found in, for example, the following published materials. A. Feldkamp, L. C. Davis, L W. Kress. Practical cone-beam algorithm. J. Optical Society of. America. A 1984, 1, pp:612–619; Yves Trouset, Didir Saint-Felix, Anne Rougee and Christine Chardenon. Multiscale Cone-Beam X-Ray Reconstruction. SPIE Vol 1231 Medical Imaging IV: Image Formation (1990); B. D. Smith, "Image reconstruction from cone-beam projections: necessary and sufficient conditions and reconstruction methods", IEEE Trans. MI4, 14–25, 1985; N. Navab et. al. Dynamic Geometrical Calibration for 3-D Cerebral Angiography. In Proceedings of SPIE Medical Conference, Newport Beach, California, February 1996; K. Andress. Fast Cone-Beam/Fan-Beam Reconstruction using the shear-scale-warp transformation. SCR Tech. Report, SCR-96-TR-565, 1996; and A Shashua. and N. Navab Relative Affine Structure: Canonical Model for 3D from 2D Geometry and Applications. IEEE Transactions on Pattern Analysis and Machine Intelligence, Vol. 18, No. 9, September 1996, pp. 873–883.

The following patent applications, whereof the disclosure is hereby incorporated by reference to the extent it is not inconsistent with the present invention, also provide background material for the present invention: CALIBRATION APPARATUS FOR X-RAY GEOMETRY, Ser. No. 08/576, 736, filed Dec. 21, 1995 in the name of Navab et al.; CALIBRATION SYSTEM AND METHOD FOR X-RAY GEOMETRY, Ser. No. 08/576,718, filed Dec. 21, 1995 in the name of Navab et al.; METHOD AND APPARATUS FOR CALIBRATING AN INTRA-OPERATIVE X-RAY SYSTEM, Ser. No. 08/940,923, filed Sep. 30, 1997 in the name of Navab; and APPARATUS AND METHOD FOR POINT RECONSTRUCTION AND METRIC MEASUREMENT ON RADIOGRAPHIC IMAGES, Ser. No. 08/940, 925, filed Sep. 30, 1997 in the name of Navab.

Feldkamp et. al., referred to in the afore-mentioned publications, proposed an approximate algorithm which has been widely accepted; Trouset et. al. proposed an algorithm based on Algebraic Reconstruction Technique (ART) that was based on two orthogonal Image Intensifier cameras carried by a specially tailored CT gantry; and an overview of cone beam reconstruction is provided in the work of Smith.

Feldkamp reconstruction technique is a generalization of the fan beam reconstruction extended to the third dimension. This method is based on filtered-backprojection. In this method, all the two dimensional projection images are first filtered, and then backprojected into the volume and combined.

In accordance with an aspect of the invention, it is herein recognized that theoretically, if the mapping between four non-collinear coplanar voxels and their pixel images is known, this 2-D transformation can be fully recovered without additional knowledge such as the X-ray projection geometry, X-ray source position, and image intensifier position. This approach for backprojection is of particular interest in conjunction with the present invention.

In the field of computed tomography, it is customary to use individual parameters of the geometry for backprojection. These parameters are computed at different calibration steps. Calibration apparatus and software that provides a transformation matrix relating each voxel in the world coordinate system to a point in the image has also been previously designed and used in order to compute a projection matrix. This matrix incorporates all the physical parameters involved in the 3-D to 2-D projection. These are the parameters that have been traditionally used in the back-projection step.

In the past, the number of the parameters used and computed in order to characterize both the geometry and the imaging parameters has been at least eleven parameters. It is herein recognized that theoretically six points including four coplanar points are sufficient for the calibration.

In accordance with an aspect of the invention, it is herein shown that one only needs to compute 8 parameters of a 2D planar transformation to calibrate the system and, in accordance with the present invention, only eight parameters of a 2D planar transformation are computed and this transformation is applied to get the backprojection onto one voxel plane. Three scale and shift parameters are then computed in order to backproject the data on to other parallel voxel planes; see the afore-mentioned K. Andress. Fast Cone-Beam/Fan-Beam Reconstruction using the shear-scale-warp Transformation. SCR Tech. Report, SCR-96-TR-565, 1996. However, these parameters result from the computed 2D transformation of the image using the four coplanar points and the position of the out of plane points of the calibration phantom. This procedure is described in more detail below.

In accordance with an aspect of the present invention, the transformation matrix has been successfully used in the backprojection step directly, without the need to know the individual physical parameters. This approach has been helpful in the following ways:

eliminating the need for running separate calibration steps;
  providing a more accurate backprojection by computing all the parameters at once, keeping the overall projection error at a minimum in a least squared sense; and
  formulating a voxel driven backprojection method based on homogeneous transformation matrices which resulted in an elegant and efficient algorithm.

If a 2D planar (or 2D to 2D or planar to planar) transformation is used instead of 3D-2D projection matrices the back-projection accuracy will be considerably increased.

The calibration process also becomes easier. This is because the 2D transformation can be computed quite precisely with a small number of correspondences between coplanar model points and their images. This is not the case for the computation of the projection matrices.

Apparatus operating in accordance with the principles of the invention realizes a representation of the exact volume to be reconstructed or a volume which includes the volume of interest. The 2D transformation therefore backprojects the image directly into a plane inside the region of interest.

In accordance with an aspect of the invention, a C-arm calibration method for 3D reconstruction in an imaging system comprising an imaging source and an imaging plane, the method utilizes a planar transformation for relating voxels in a voxel space and pixels in the imaging plane, and comprises the steps of: defining a source coordinate system in reference to the imaging source.

In accordance with another aspect of the invention, defining a normal plane in the voxel space, not including the origin of the source coordinate system and being substantially normal to an optical axis from the source to the imaging plane; defining a relationship between the source coordinate system and another coordinate system, herein referred to as a world coordinate system, by transformation parameters; identifying pixel location coordinates for a respective pixel corresponding to each voxel by utilizing planar to planar transformation parameters; storing a value of a filtered image at the respective pixel location; accumulating contributions corresponding to a plurality of image projections so as to thereby reconstruct the each voxel; dividing the voxel space into a plurality of planes not parallel to the normal plane; back projecting an image of a plurality of pixels on the image plane onto a set of coplanar voxels defining one of the plurality of parallel planes; and defining a relationship in the source coordinate system between each of the plurality of pixels and corresponding ones of the coplanar voxels so as to obtain a 2-dimensional mapping between points on the one of the plurality of planes and pixels on the image plane.

In accordance with another aspect of the invention, the plurality of planes comprises 3 planes in addition to the normal plane.

In accordance with another aspect of the invention the plurality of planes comprises 3 planes forming, together with the normal plane, an intersection along one line.

In accordance with another aspect of the invention the plurality of planes and the normal planes are separated by consecutive angles of 45 degrees.

In accordance with another aspect of the invention, the plurality of pixels on the image plane comprises at least 4 pixels.

In accordance with another aspect of the invention a step is included of imaging 2 further voxels outside of the one of the plurality of parallel planes, whereby coordinate information is obtained defining a position for the source in terms of the 2-dimensional mapping.

In accordance with another aspect of the invention a step is included of deriving values for the transformation parameters from the coordinate information.

In accordance with an aspect of the invention, a C-arm calibration method for 3D reconstruction in an imaging system comprising an imaging source and an imaging plane, the method utilizes a planar transformation for relating voxels in a voxel space and pixels in the imaging plane, and comprises the steps of: defining a source coordinate system in reference to the imaging source; In accordance with another aspect of the invention defining a normal plane in the voxel space, not including the origin of the source coordinate system and being substantially normal to an optical axis from the source to the imaging plane; defining a relationship between the source coordinate system and another coordinate system, herein referred to as a world coordinate system, by transformation parameters; identifying pixel location coordinates for a respective pixel corresponding to each voxel by utilizing the planar to planar transformation parameters; storing a value of a filtered image at the respective pixel location; accumulating contributions corresponding to a plurality of image projections so as to thereby reconstruct the each voxel; dividing the voxel space into a plurality of planes not parallel to the normal plane; back projecting an image of a plurality of pixels on the image plane onto a set of coplanar voxels defining one of the plurality of parallel planes; and defining a relationship in the source coordinate system between each of the plurality of pixels and corresponding ones of the coplanar voxels so as to obtain a 2-dimensional mapping between points on the one of the plurality of planes and pixels on the image plane.

In accordance with another aspect of the invention, the plurality of planes comprises 3 planes in addition to the normal plane.

In accordance with another aspect of the invention the plurality of planes comprises 3 planes forming, together with the normal plane, an intersection along one line.

In accordance with another aspect of the invention the plurality of planes and the normal planes are separated by consecutive angles of 45 degrees.

In accordance with another aspect of the invention, the plurality of pixels on the image plane comprises at least 4 pixels.

In accordance with another aspect of the invention a step is included of imaging 2 further voxels outside of the one of the plurality of parallel planes, whereby coordinate information is obtained defining a position for the source in terms of the 2-dimensional mapping.

In accordance with another aspect of the invention a step is included of deriving values for the transformation parameters from the coordinate information.

The invention will next be described by way of exemplary embodiments with the aid of the Drawing, in which FIG. 1 shows cone-beam reconstruction parameters;

It will be understood that the data processing and storage as performed at various steps and portions of the present invention is best carried out by a general purpose programmable computer and that images are intended to be rendered visible where required by processing stored or real time data in apparatus of known type for performing such a function, as is known in the art. A special purpose or dedicated computer may also be used. Generally, the application of a digital computer for image processing as such in conjunction with X-ray imaging apparatus for backprojection is well-known in the art and need not be detailed here since the arrangement of such a setup can be readily found in the literature. Where a particular storage or data processing function is specified, it will be understood that a properly programmed computer is so modified or programmed by instruction as to constitute an effective apparatus for performing the processing or storage.

It will also be understood that calibration procedures and the determination of a geometry generally involve the use of a phantom structure to provide the necessary reference points in a voxel space and the related images to which they are being related. Thus, for example, it is understood that a step of defining a coordinate system in relation to an imaging source typically involves the use of a phantom.

The concept of backprojection is of significance to the present invention. Filtered-Backprojection techniques including Feldkamp reconstruction have been developed in the field of CT. Accordingly, different implementations have been greatly influenced by the existing traditional implementations. Typically, physical parameters of the system are used in the backprojection.

Figure 1:
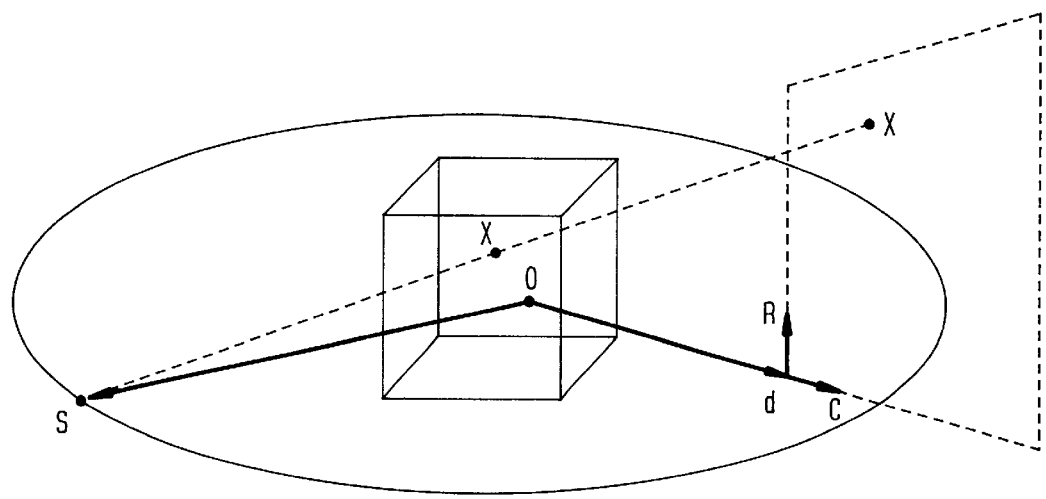

For cone beam reconstruction these parameters are illustrated in FIG. 1. $\vec{s}$ is the X-ray source that is moving on an orbit around the center of rotation O. $\vec{d}$ is a vector connecting the center of rotation to the origin of the two dimensional detector. $\hat{R}$ and $\hat{C}$ are two unit vectors signifying the orientation of the orthogonal axes on the detector plane More recently, there has been interest in a voxel oriented approach to backprojection, as previously described. As explained, this approach involves tracing a ray from the X-ray source $\vec{s}$ to a voxel $\vec{X}$ and continued until it intersects the image intensifier at point $\vec{x}$, marking the point by which the voxel is affected during the backprojection step.

The 3D reconstruction from multiple views has been a subject of interest both in photogrammetry and computer vision, in photogrammetry since the beginning of the 20$^{th}$ century and in computer vision since 1960s. In medical imaging this has became a subject of increasing importance during the last decades. Even if the reconstruction problem in medical imaging appears rather different, very often similar mathematical interest in the problem of reconstruction from a set of X-ray images.

Figure 2:
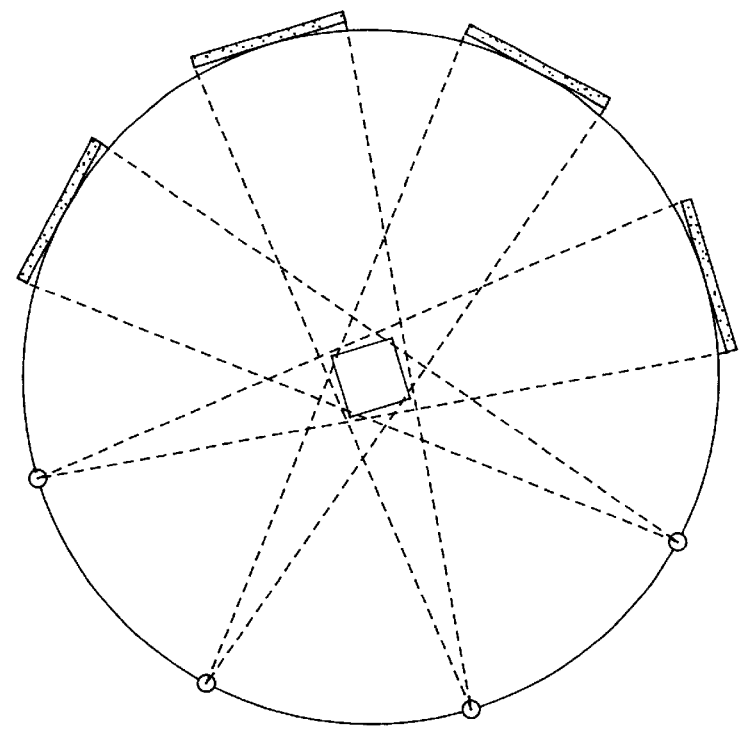
FIG. 2 shows C-arm motion.

A C-arm mounted XRII typically rotates more than 180 degrees, typically 200 degrees, around the object of interest and takes about one hundred radiographic images. This is shown in FIG. 2. When the motion of the C-arm, and the characteristics of the image intensifier are known, the reconstruction can be done, for example, by filtered-backprojection.

In the traditional computed tomography reconstruction, the motion of the C-arm, the relation between the X-ray source and the image intensifier, and the pixel size are computed in different steps. These quantities are later used in the mathematical formulation in order to form the full backprojection geometry, from image coordinates in pixels to 3D coordinates in voxels (for example, in millimeters). In the field of computer vision, for points or line reconstruction, the projection matrices have been frequently used directly without decomposing them into different parameters. This is done when the correspondences between image features, such as corner points or edge lines are given over multiple images. The same has been done in the case of backprojection. Mapping is needed between 3D voxel coordinates and 2D pixel coordinates.

If the pinhole camera be taken as a model for the X-ray imaging system this mapping can simply be written as:

$$\bar{x} = P\bar{X} \qquad \text{Equation 1}$$

where $\bar{x}=[u,v,1]$ and $\bar{X}=[x,y,z,1]$ are the homogeneous coordinates of the image pixel and 3D voxel in the canonical homogeneous coordinate system. The symbol is used to emphasize that the equality is in homogeneous coordinates and therefore up to scale.

Figure 3:
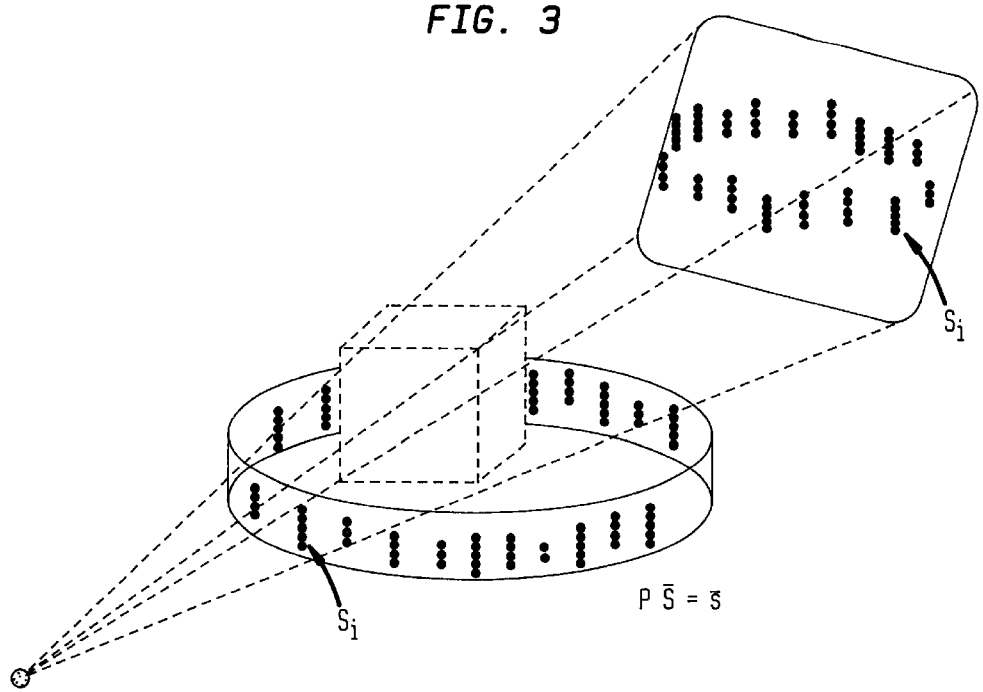
FIG. 3 shows a calibration system.

It has been shown that the backprojection can be done without decomposing the matrix P and therefore without explicit knowledge of (1) the C-arm motion such as orientation and position, and (2) the imaging parameters such as image center and scales along row and columns. This is apparent from Equation I which defines the 3D/2D mapping all together. The main reason this had not been used sooner, is most probably because these parameters were computed through different processes and researchers s would not see the advantage of formulating the backprojection based on projection. A calibration system was designed using uniquely identifiable markers positioned on a cylinder. This system is illustrated in FIG. 3. This calibration ring comprises steel balls positioned in a predefined arrangement on a cylindrical acrylic allowing the computation of the backprojection matrices. See the above-mentioned patent applications Ser. Nos. 08/576,736 and 08/576,718. In this way the projection matrices or the 3D/2D mapping function are directly computed.

First, it will be shown that the back-projection process, a 2D-3D mapping, can be replaced by a set of 2D projective transformations, 2D-2D mappings. This means that instead of doing 3D-2D or 2D-3D mapping, in accordance with the principles of the invention simple image warping processes are preferably utilized in order to obtain the same result. The difference is that it is easier to compute these 2D projective transformations and they can be computed with much higher accuracy than the accuracy of the computation of the projection matrices.

In addition, because of the extended use of image warping in different applications, including 3D graphics and visualization for entertainment and video game industry, during the last few years many hardware solutions have become available for accelerating this process, and for doing it in real time. In the following section, the 3D-2D transformation matrices, the 2D-2D, and their mutual relationship transformation matrices are described.

There follows next a description of the backprojection geometry using one planar transformation. First, define the camera coordinate system as generally defined in the computer vision art. In the camera coordinate system the X-ray source is the origin. The z-axis is along the optical axis, and the images center and the pixel size are defined in order to have a perfect pinhole model. In this case P=[I,0], where I is the 3×3 identity matrix and 0 is a null vector of dimension three. Therefore in the camera coordinate system x=zu and y=zv. When the matrix of the projection is defined in a coordinate system other than the camera coordinate system, it is necessary to first apply a rotation R followed by a translation T to relate the location and orientation of the two coordinate systems. The parameters defining R, and T are called the extrinsic parameters (also transformation parameters), because their values depend only on the location and orientation of the imaging system relative to the other coordinate system, usually called the world coordinate system. The imaging parameters called the intrinsic parameters are then taken into consideration. These are the image center [u0, v0] and the horizontal and vertical scales $\alpha_u$ and $\alpha_v$. Therefore it follows that:

$$P = [AR\ AT] \quad \text{Equation 2}$$

$$\text{where } A = \begin{bmatrix} \alpha_u & 0 & u_0 \\ 0 & \alpha_v & v_0 \\ 0 & 0 & 1 \end{bmatrix}$$

The matrix A allows the 3D point to be mapped directly onto the image plane (pixel coordinates). This matrix incorporates scaling along the horizontal and vertical directions due to digitization process. It also incorporates shifting of the coordinate center from the image center (intersection of optical axis with the image plane) to an arbitrary point on the image.

The parameters $\alpha_u$ and $\alpha_v$ convey the horizontal and vertical scaling of the digitization process. It is important to note that the matrix P relates every 3D point in the world coordinate frame to a pixel in the image (computer memory).

Figure 4:
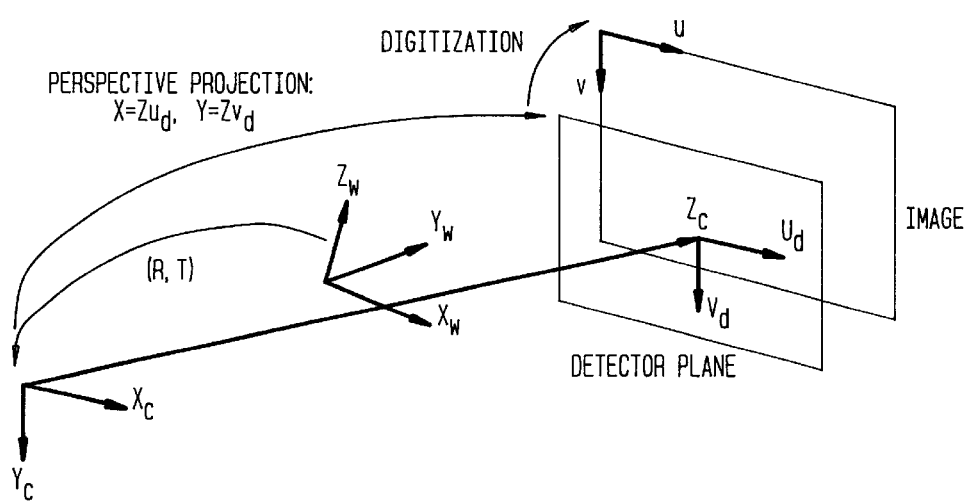
FIG. 4 shows an imaging process.

FIG. 4 illustrates the imaging process including: (a) going from a point in the world coordinate system ($X_w$, $Y_w$, $Z_w$) to a camera coordinate system ($X_c$, $Y_c$, $Z_c$), (b) perspective projection onto the detector plane, and (c) the digitization process and change of coordinate center to an arbitrary point (upper left corner).

Once the mapping between a voxel and a pixel has been defined, the backprojection process can be simplified by using Equation 1. Every voxel can then be reconstructed by:
1. finding its pixel coordinates in every projection using Equation 1;
2. taking the value of filtered image at that pixel coordinate (by interpolation, nearest neighbor, etc.); and
3. accumulating contributions from each projection (either by adding them up, or by using any other combination rule such as evidence accumulation).

Figure 5:
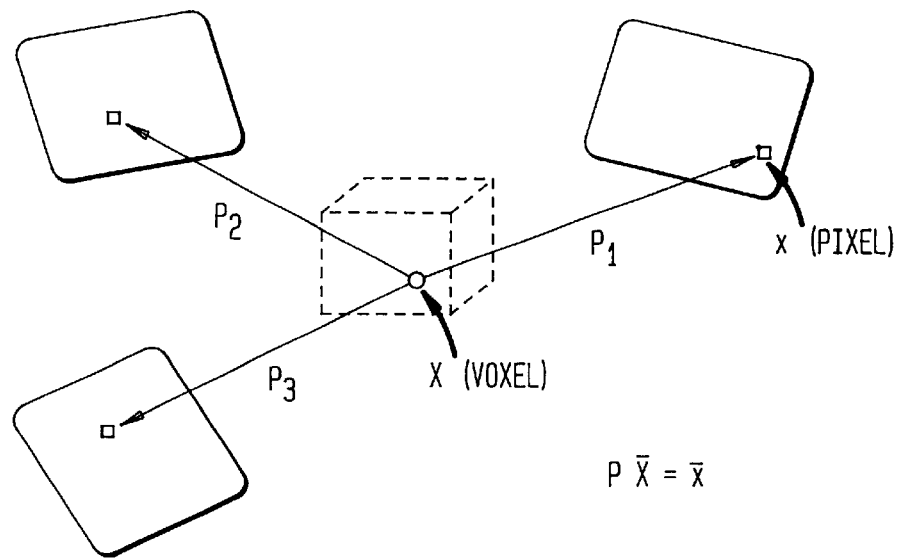
FIG. 5 illustrates backprojection from multiple projections onto a voxel.

FIG. 5 illustrates the backprojection from multiple projections onto a voxel. The matrices $P_i$ could be the direct outcome of a calibration process, and they project the voxels onto their corresponding projection images. This calibration process provides a one step solution which can compute all the relevant information for the backprojection process. This eliminates the need for separate calibration procedures for computing different system parameters.

It will be shown that the backprojection can be carried out in accordance with the principles of the invention by computing a 2D planar transformation and two dimensional scale and shift parameters. The computation of this transformation can be done with much higher accuracy than the direct computation of the projection matrices.

First, divide the voxel space into a set of parallel planes. It is desired to backproject the radiographic image on to a set of coplanar voxels defining one of the said parallel planes.

Working now in a coordinate system attached to the X-ray source, where the z-axis is parallel to the optical axis (the normal dropped from the X-ray source onto the image plane), and the x-axis and y-axis are parallel respectively to the image row and columns, a plane π is defined, not including the origin of the coordinate system, by the normal to the plane n and its signed distance from the origin. d . For each point (voxel) on this plane, the following obtains: $n^t X/d=1$. For each voxel on the plane π, the projection equation 1. and the equation 2. both written in this new coordinate system result in:

$$\bar{x} \cong P\bar{X} = [AR\ AT]\bar{X} =$$

$$ARX + AT = ARX + \frac{ATn^t X}{d} = \left(ARX + \frac{ATn^t X}{d}\right)X \cong HX \cong \bar{x}'$$

This defines a 2D planar transformation H which can be computed accurately using the correspondences between a set of planar points (minimum four points) and their images. Note that, in accordance with the principles of the invention, it is not necessary to know the 3D coordinates of these planar points. Their relative position within their common plane is sufficient to compute this 2D planar transformation.

Therefore, if $\bar{x}'=[u', v',1]$ is the homogeneous coordinates of a point (voxel) written in an arbitrary 2D coordinate system defined on a plane π, there is a direct 2D-2D mapping between the points on this plane and the homogeneous coordinates of the image pixels $\bar{x}=[u,v,1]$. Thus, $\bar{x}=H\bar{x}'$, where H is a 3×3 homogeneous matrix defining this 2D planar transformation.

Note that a change of coordinate system in the plane π can be introduced by multiplication of the transformation matrix by a 3×3 invertible matrix. This will change the matrix H but there will still be a 3×3 matrix of planar transformation. It will not therefore change either the computation or the nature of the procedure. There are eight parameters to be recovered and 4 point correspondences between the voxel plane, and the image plane are theoretically sufficient for the estimation of this mapping. When more than four points correspondences are available a least-squares minimization results in a more accurate mapping. These kinds of 2D transformations have been used in different applications, such as texture mapping, relative affine reconstruction, and motion estimation. These are known to be quite precise and reliable. In addition they can be easily implemented in hardware, and they can also be implemented using many available texture mapping hardware.

In the previous paragraph it was shown that the backprojection from image plane onto a set of planar voxels can be done through a 2D transformation H. Here it will be shown that if two points out of this plane are also imaged by the system, computing the 2D transformation H and applying it to the image including the image of these two points results in the full recovery of the projection geometry.

Figure 6:
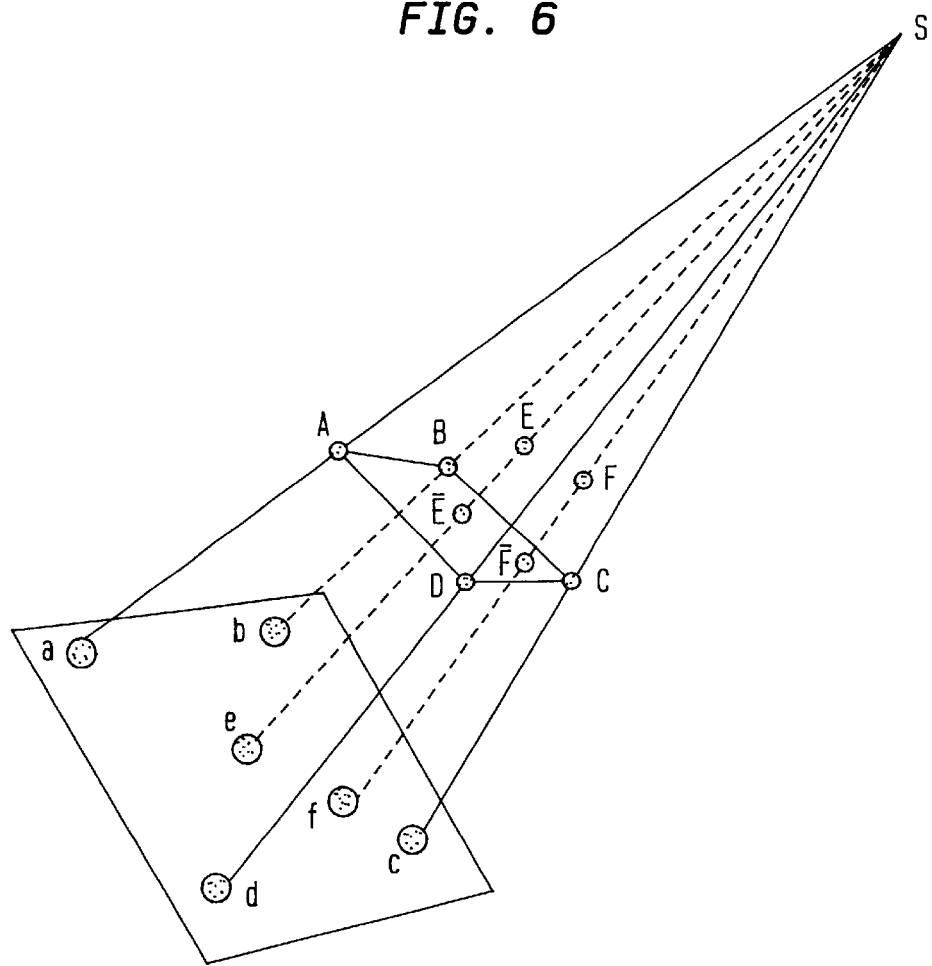
FIG. 6 shows a projection geometry for four coplanar points.

FIG. 6 illustrates such a scenario. The point A, B, C, and D are on a plane π. The points E and F are outside this plane at known positions relative to the four coplanar points A, B, C, and D.

Next the 2D planar transformation H which maps the four image points a, b, c, and d in FIG. 6, to the four coplanar points A, B, C, and D, and apply this transformation H to the image points e, and f are computed. The resulting points $\overline{E}$=He and $\overline{F}$=Hf are by construction the intersection of the rays $\overline{SE}$ and $\overline{SF}$, S being the X-ray source position, and the plane π defined by A, B, C, and D. It is herein recognized that this allows a straight forward computation of the X-ray source position illustrated in FIG. 7.

Figure 7:
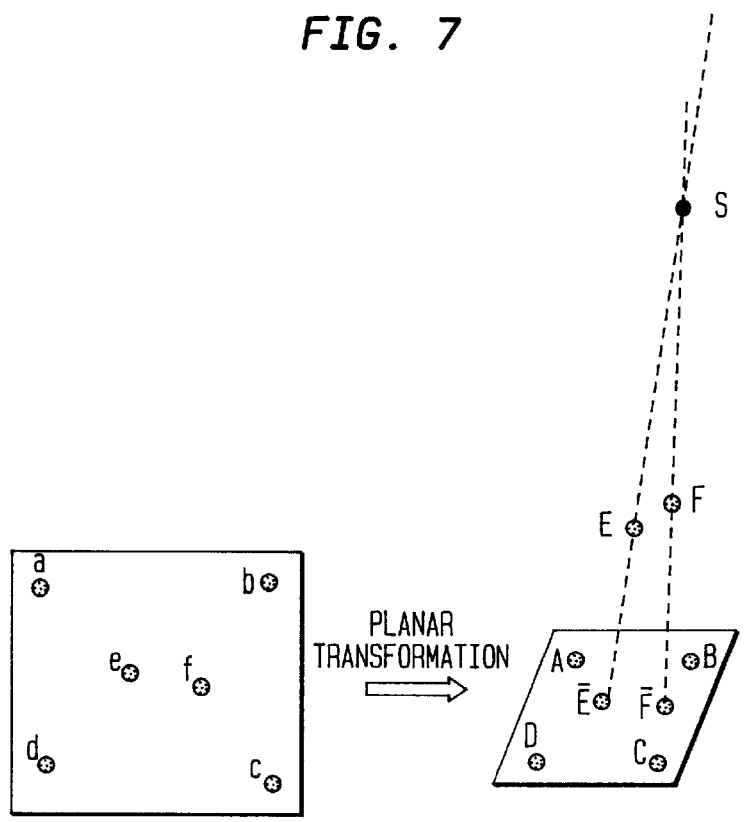
FIG. 7 shows recovery of the X-ray source position using planar transformation.

The planar transformation H is first computed using the correspondences between the coplanar points and their images, e.g. A, B, C, and D, and their images a, b, c, and d in FIG. 7. This planar transformation H is then applied to the images of the points which are not on the same plane, e.g. $\overline{E}$=He and $\overline{F}$=Hf. These points are then connected to their corresponding 3D points. The intersection of these vectors defines the X-ray source position, e.g. X-ray position S in FIG. 7 is at the intersection of the rays $\overline{SE}$ and $\overline{SF}$. Once the position of the X-ray source is computed, the position of the iso-center can also be computed by computing the center of the circle defined by the consecutive X-ray positions during the C-arm motion. The axis of rotation can also be computed using the planar transformations computed during the C-arm motion. If a pure rotational motion R is applied to the C-arm, the planar transformation H and H' computed before and after motion have the simple relationship H=RH', this provides a simple system of equations to be solved in order to computed this rotation and therefore the axis of rotation. In the general case where an iso-center or a unique axis of rotation does exist, the above computation provides an estimation of these in a least squares sense.

Once the image is backprojected onto one voxel plane π, it is necessary to backproject it also to all other voxel planes in the voxel volume to be reconstructed. If the voxel volume be divided into planes parallel to the reference plane π, Andress, cited above, has shown that the motion between the backprojected images onto the plane π and another parallel plane can be defined by a shift followed by scaling. This means that $H_i$ the planar transformation between the X-ray image and any plane $\pi_i$ parallel to the plane π, is defined by $H_i=\lambda H$:

$$\text{where } \lambda = \begin{bmatrix} \kappa & 0 & x_0 \\ 0 & \kappa & y_0 \\ 0 & 0 & 1 \end{bmatrix}.$$

where the change of scale is defined by κ and the shift by $x_0$ and $y_0$.

Figure 8:
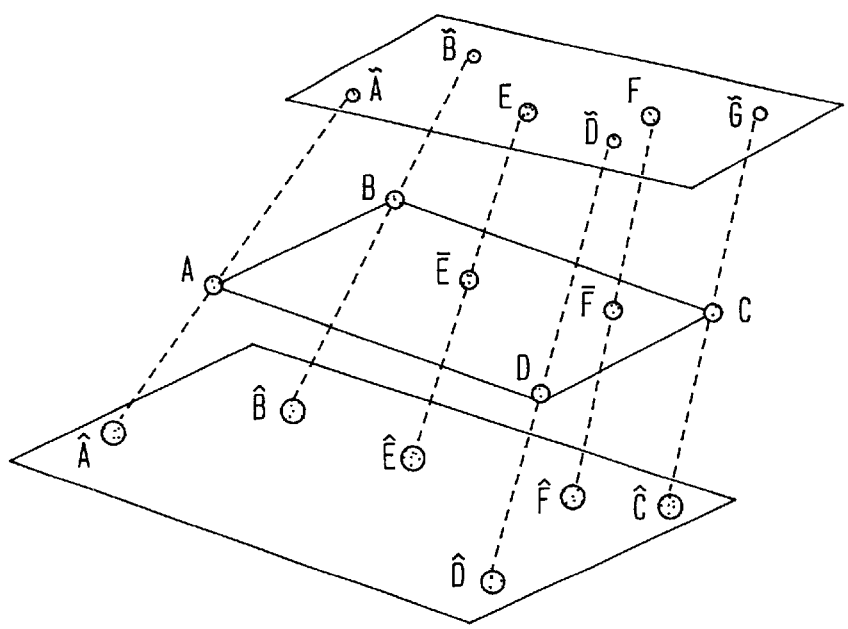
FIG. 8 shows correspondences between images of out of plane points.

These parameters, κ, $x_0$ and $y_0$, can be readily computed by solving a system of linear equations describing the motion of the out of plane points, e.g. solving the system of equations defined by $\overline{E}=\lambda \overline{E}$ and $\overline{F}=\lambda \overline{F}$ for the three parameters of λ. For each plane $\pi_i$, parallel to the plane π, it is preferred to use the correspondences between the images of the out of plane points, e.g. $\overline{E}$ and $\overline{F}$, and the intersection of the planes $\pi_i$ and the lines defined by these image points and their corresponding 3D model points, e.g. in FIG. 8 points $\hat{E}$ and, $\hat{F}$ are the intersection of the lines defined by $E\vec{E}$ and $F\vec{F}$ and a plane parallel to the reference plane.

Figure 9:
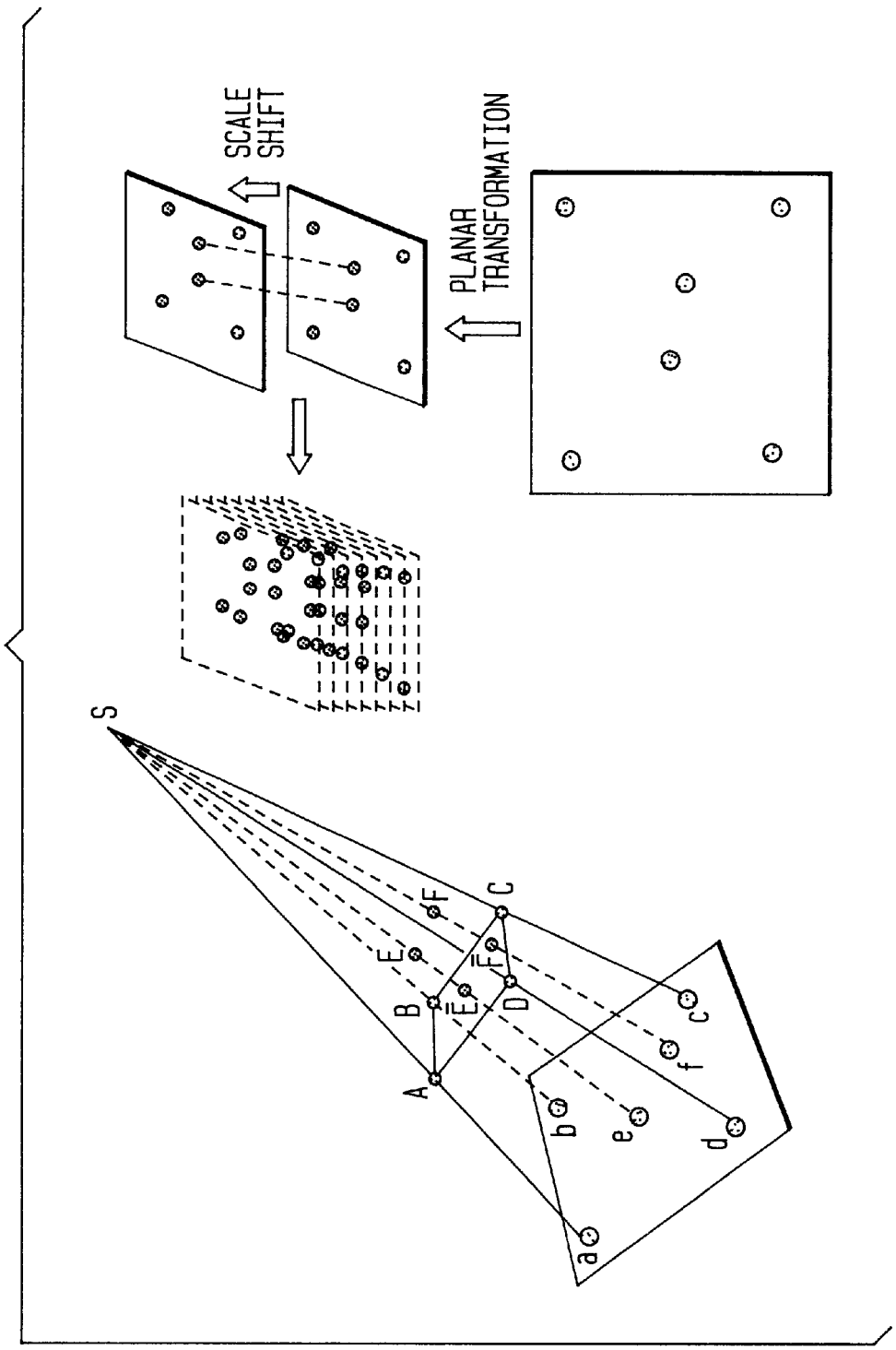
FIG. 9 shows a backprojection principle visualized on a calibration phantom.
Figure 10:
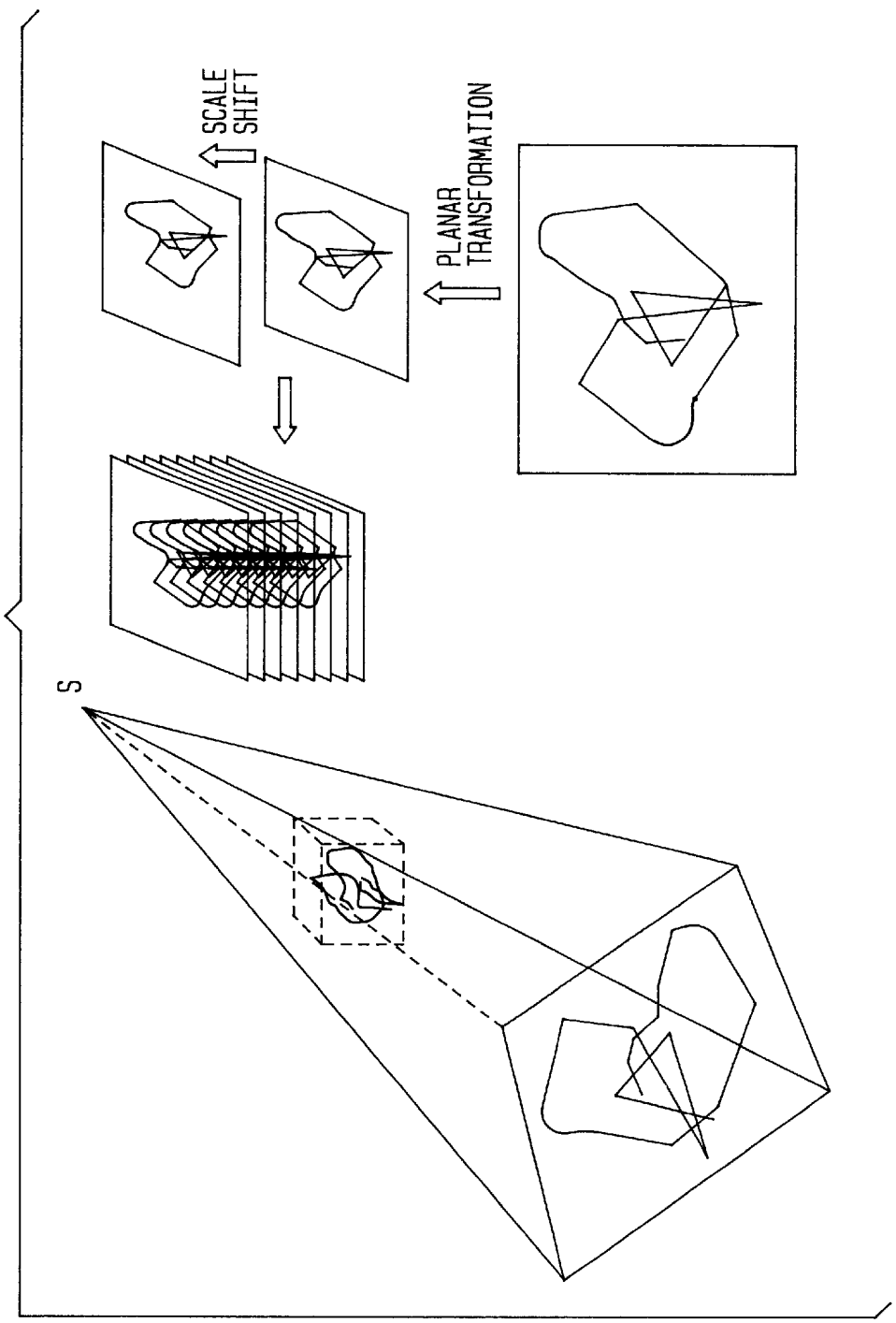
FIG. 10 shows the backprojection principle during a patient run.

FIG. 9. illustrates this principle with the calibration phantom points in the off-line calibration process, and FIG. 10 represents the same backprojection process during the patient run.

In accordance with the present invention a calibration method and apparatus to be used in conjunction with the computation and use of 2D planar transformations in order to do the necessary backprojection needed for the 3D reconstruction are described by way of an exemplary embodiment. In the previous section it was explained that four coplanar points and two points out of this plane at least are necessary to enable a computation of the geometry and proceed to the backprojection process for reconstruction. Beginning with a plane $\pi_i$ approximately parallel to the image intensifier, as the X-ray source and image intensifier rotate around the calibration phantom, the angle between the image intensifier plane and plane $\pi_i$, t, increases and the 2D mapping between the image plane and the plane $\pi_1$ becomes less accurate until the C-arm makes near 180 degrees rotation and the two planes become once again approximately parallel. The 2D mapping is quite accurate when the calibration plane $\pi_i$ is parallel to the image intensifier. It gets less accurate as the angle between the image intensifier and the calibration plane $\pi_i$, increases.

Figure 11:
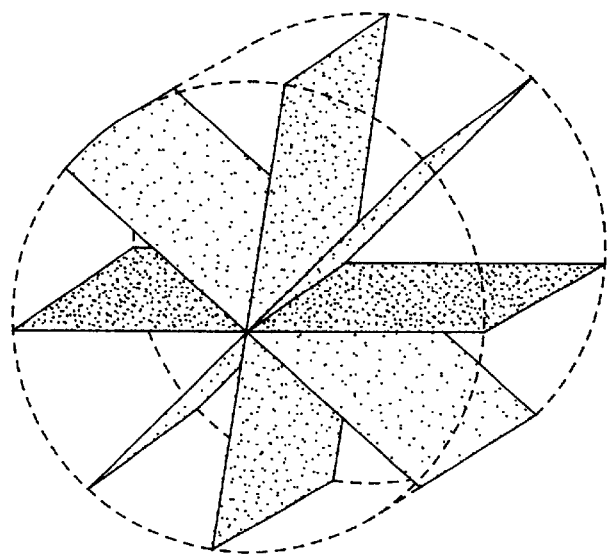
FIG. 11 shows four planes intersecting in one line and separated by consecutive angles of 45 degrees in accordance with the present invention.

In order to increase the accuracy of the computation of the planar transformations, other planes can be added non parallel to the first plane $\pi_i$. FIG. 11 illustrates a calibration apparatus comprising four planes intersecting in one line and separated by consecutive angles of 45 degrees each.

It will be understood that the markers are opaque, the planes are substantially transparent.

Figure 12:
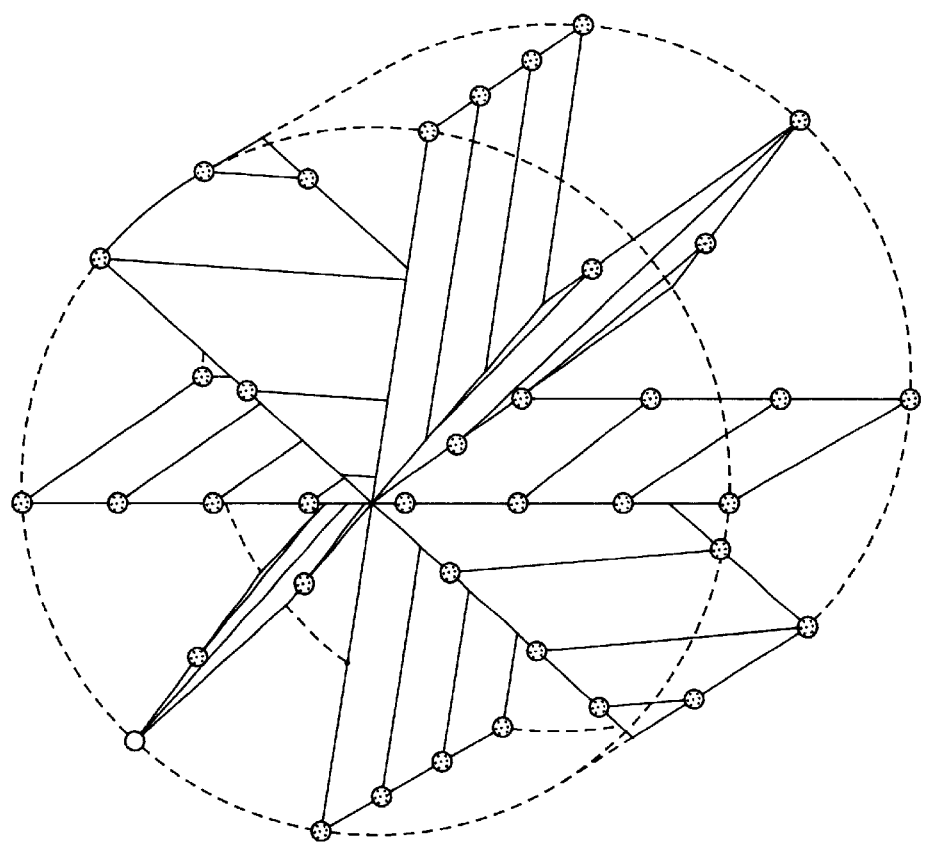
FIG. 12 shows calibration patterns on the intersecting planes selected such that detection of coplanar markers is possible even though all the patterns will be superimposed on the radiographic images.

In order to enable the system to detect automatically the markers on each plane and be able to compute the 2D planar transformations, special calibration patterns are put on each of these planes such that the detection of coplanar markers is possible even though all these patterns will be superimposed on the radiographic images. FIG. 12 illustrates an example of such design. Note that both spheres and lines are designed to be opaque to X-rays.

Figure 13:
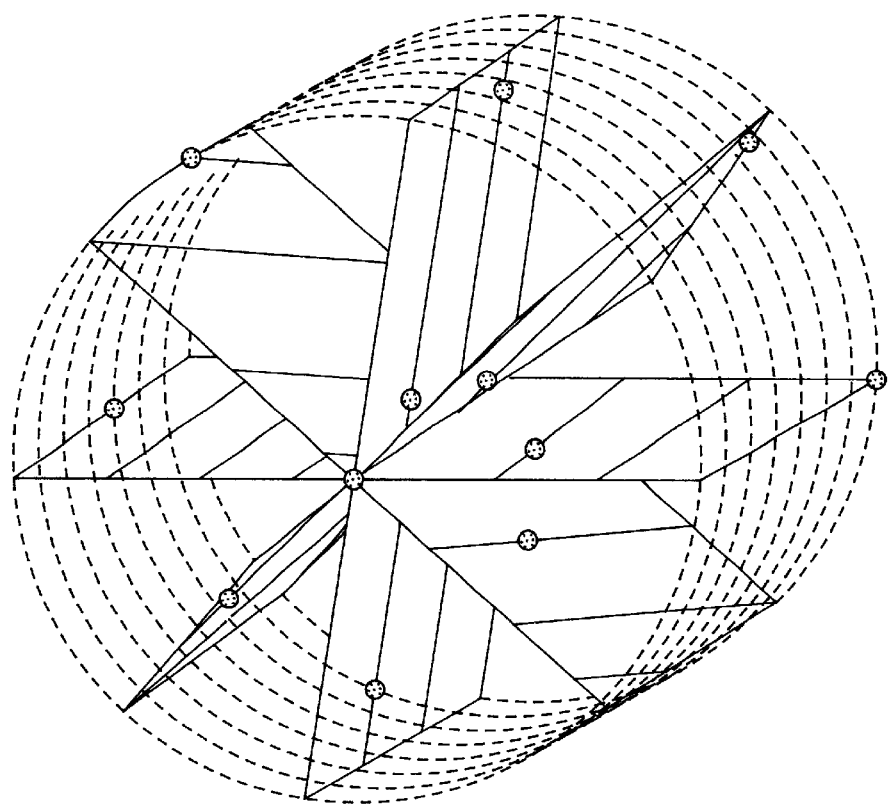
FIG. 13 shows spherical markers positioned along linear features on the four planes and on different planes orthogonal to the intersection of the planes.
Figure 14:
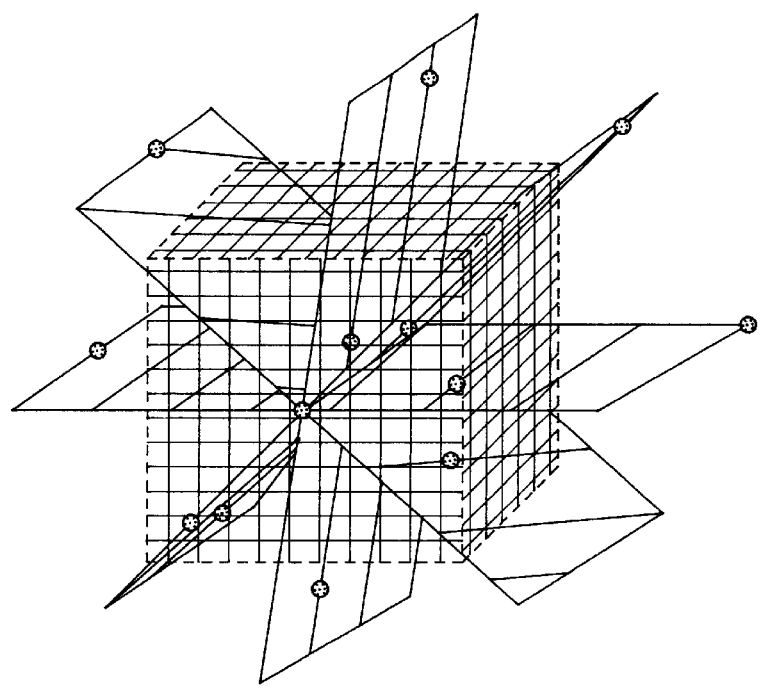
FIG. 14 shows an ideal relative position of a phantom and the voxel volume to be reconstructed.

In order to reduce the chance of the radiographic images of the spherical markers getting superimposed one on top of another, they are positioned on different planes orthogonal to the intersection line of all four planes, and the calibration phantom is positioned such that this axis is as much as possible parallel to the axis of rotation of the C-arm. This can be done by moving the patient table such that the main axis of the calibration phantom, i.e. the intersection of the four planes, stays approximately in the same position. Note that this has not to be done accurately and is not a necessary condition. The final calibration phantom would therefore can be approximately illustrated as in FIG. 13, in accordance with this exemplary embodiment.

All the planes, lines and points, i.e. center of spheres, are known by construction in a common coordinate system. For each radiographic image one or multiple planes will be used for the computation of one or more planar transformations. In the case where only one plane is used, the plane which makes smallest angle to the image plane is used; a parallel plane is optimum, and is chosen to compute the reference planar transformation. The image of a square would be a square if it is parallel to the image plane; the amount of deviation from this plane, in order to choose the best reference plane, can be measured by the deformation of the shape. In this case all or some, at least two, of the reliably detectable points on the other three planes are used in order to compute the scale and shift parameters; see the previous section for details of the estimation of the back-projection geometry. In the case more than one plane is used; the same process is repeated for each reference plane and the back-projection will be obtained by combining these two back-projections. In this case the backprojection results can be combined such that a reference plane which is parallel to or makes a smaller angle with the image intensifier contributes more to the final back-projection result.

Figure 15:
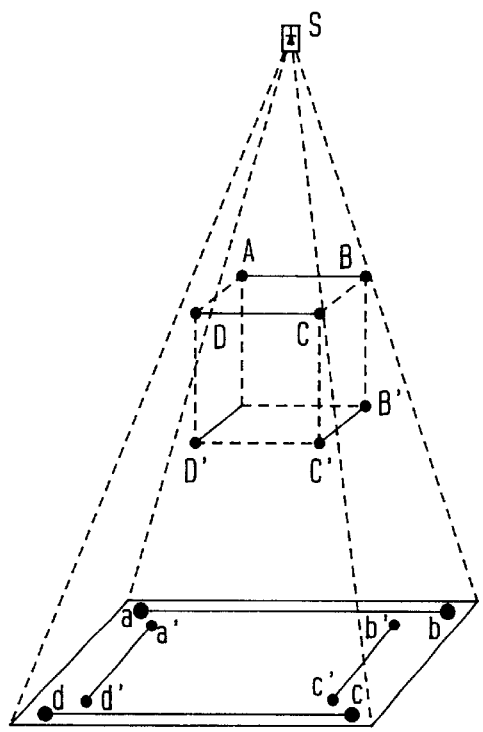
FIG. 15 shows two parallel planes projected onto the image plane.

There follows next a description of a system utilizing two planar transformations. Another option is to use two parallel reference planes instead of one. In this case the scale and shift estimation is not used. The 2D transformations between the two parallel planes and the radiographic image are used to backproject the radiographic image into the two planes and all other planes parallel to these planes. FIG. 15 shows two parallel planes projected onto the image plane.

Figure 16:
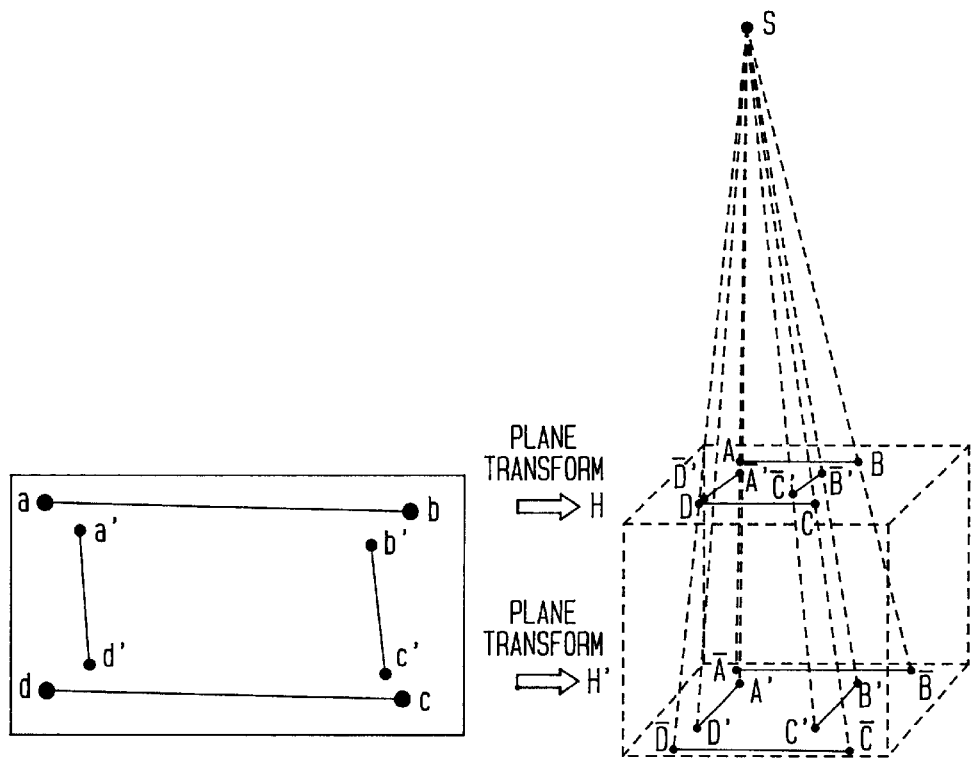
FIG. 16 shows 2D transformations H and H' for two parallel planes.

FIG. 16 illustrates the two 2D transformations H and H' for two parallel planes. It also shows that similarly to what is described in the previous section the X-ray source position can be obtained using each planar transformation and the transformation of the points out of these planes by this transformation. In this figure all the vectors $A\overline{A}$, $B\overline{B}$, $C\overline{C}$, $D\overline{D}$, $A'\overline{A}'$, $B'\overline{B}'$, $C'\overline{C}'$, and $D'\overline{D}'$ theoretically intersect at the X-ray source position S.

The computation of the axis of rotation, when the approximation of a pure rotational motion is taken, is also similar to the previous section. The only difference is that since here there are two planes undergoing the same rotation, use both corresponding planar transformations can therefore be used in order to get a more accurate computation of rotational motion and therefore more accurate average axis of rotation. The backprojection is formulated such that all voxels inside the cube defined by the two planes in FIG. 16 can be mapped into their corresponding pixel on the image using the two planar transformations H and H'. In order to combine these results all these points are projected onto each plane parallel to the reference planes, e.g. by intersecting $A\overline{A}$, $B\overline{B}$, $C\overline{C}$, $D\overline{D}$, $A'\overline{A}'$, $B'\overline{B}'$, $C'\overline{C}'$, and $D'\overline{D}'$ with this plane, and computing one planar transformation between the radiographic image and this plane. In order to correctly combine the information of the two reference planes this information is weighted inversely proportional to the distance of this current plane from the reference plane from where the information originated, e.g. the equations involving the intersection of A $\overline{A}$ and this new plane are weighted inversely proportional to the distance of the plane from the reference plane containing the point A.

Figure 17:
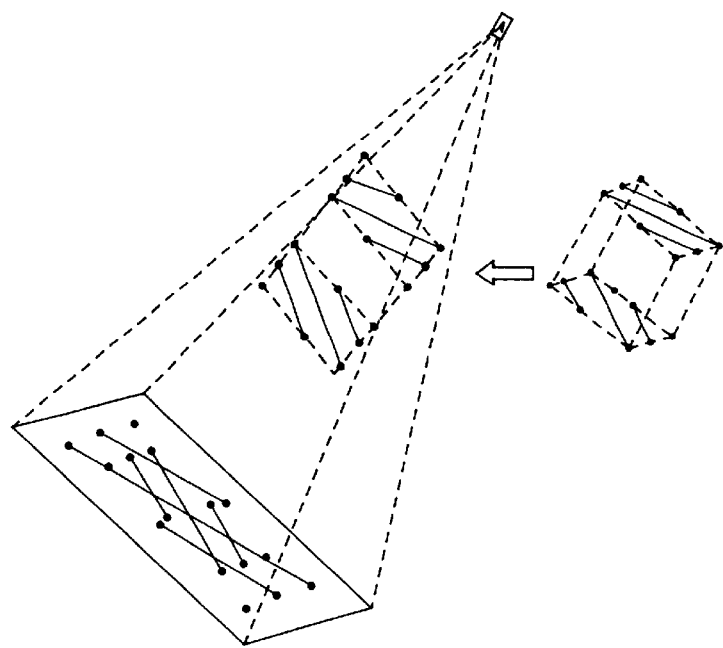
FIG. 17 shows a 45 degree rotated cube to be added to the calibration phantom.
Figure 18:
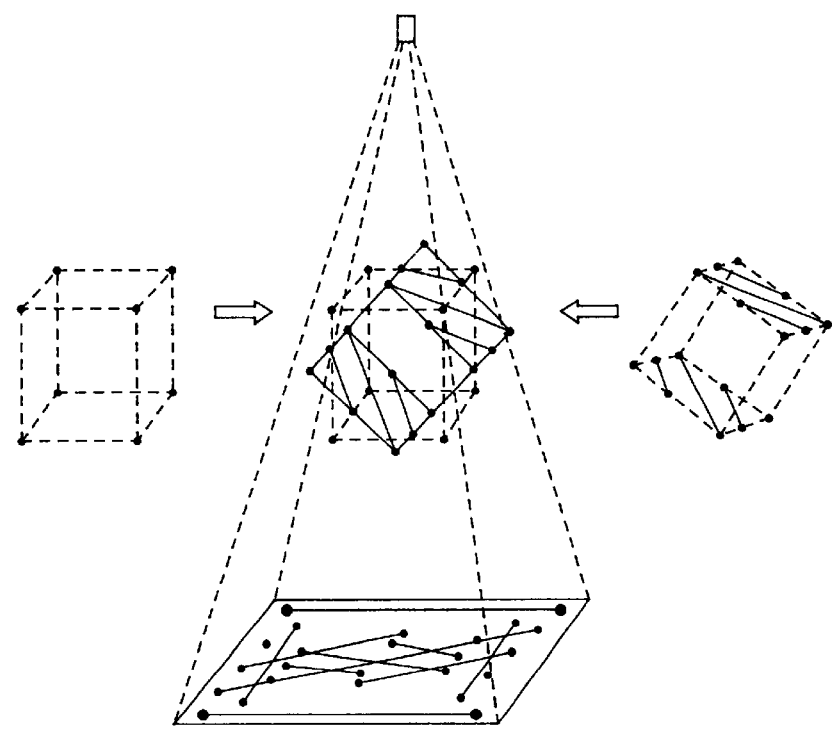
FIG. 18 shows a possible phantom with two cubes.

As the X-ray source and image intensifier rotate around the calibration cube, the 2D mappings become less accurate. These mappings are quite accurate when the reference sides of the calibration cube are parallel to the image intensifier. They get less accurate as the angle between the image intensifier and these sides of the calibration cube increases. In order to increase the accuracy of the computation of the planar transformations, other planes can also be added non parallel to the voxel cube. FIG. 17 illustrates a 45 degrees rotated cube to be added to the calibration phantom: FIG. 18 shows a possible phantom with the two cubes.

Figure 19:
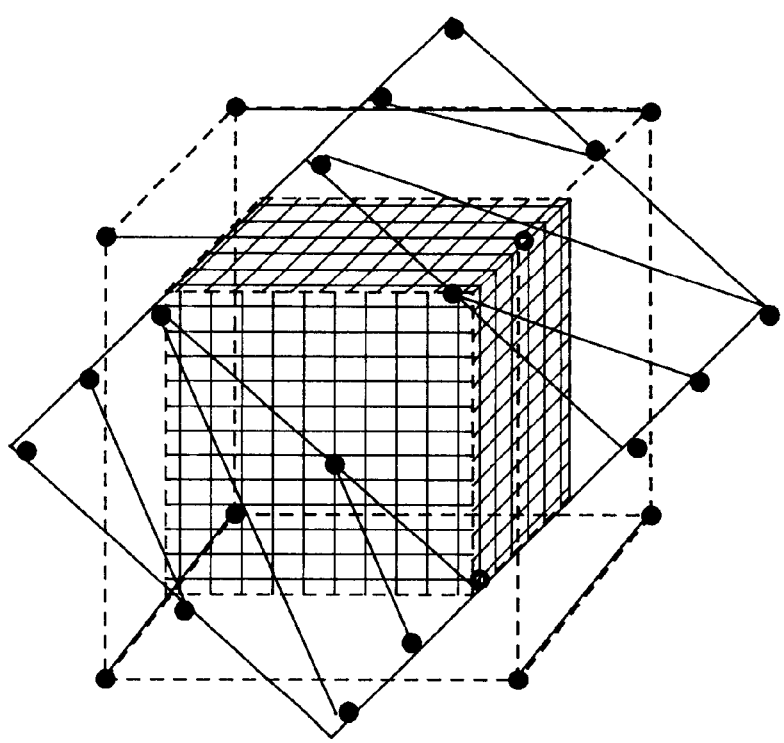
FIG. 19 shows a calibration phantom including and centered about the volume of interest, in accordance with the invention.

In this case once again the best positioning is to have the common axis of the two cubes approximately passing through the iso-center and parallel to the axis of rotation. The phantom should also be as much as possible centered around the center of the volume of interest, see FIG. 19.

Similar to the previous section the spherical markers can also be positioned in different planes orthogonal to the axis of rotation of the two cubes in order to minimize the risk of having the image of the spherical markers getting superimposed.

The present invention has been described by way of exemplary embodiments. It will be understood by one skilled in the art to which it pertains that various changes and modifications can be made without departing from the scope and spirit of the invention which is defined by the claims following.

What is claimed is:

1. A C-arm calibration method for 3D reconstruction in an imaging system comprising an imaging source and an imaging plane, said method utilizing a planar transformation for relating voxels in a voxel space and pixels in said imaging plane, and comprising the steps of:

defining a source coordinate system in reference to said imaging source;

defining a normal plane in said voxel space, not including the origin of said source coordinate system and being substantially normal to an optical axis from said source to said imaging plane;

defining a relationship between said source coordinate system and another coordinate system, herein referred to as a world coordinate system, by transformation parameters;

identifying pixel location coordinates for a respective pixel corresponding to each voxel by utilizing planar to planar transformation parameters;

storing a value of a filtered image at said respective pixel location;

accumulating contributions corresponding to a plurality of image projections so as to thereby reconstruct said each voxel;

dividing said voxel space into a plurality of planes parallel to said normal plane;

back projecting an image of a plurality of pixels on said image plane onto a set of coplanar voxels defining one of said plurality of parallel planes; and defining a relationship in said source coordinate system between each of said plurality of pixels and corresponding ones of said coplanar voxels so as to obtain a 2-dimensional mapping between points on said one of said plurality of planes and pixels on said image plane.

2. A C-arm calibration method in accordance with claim 1, wherein said plurality of planes comprises 3 planes in addition to said normal plane.

3. A C-arm calibration method in accordance with claim 1, wherein said plurality of planes comprises 3 planes forming, together with said normal plane, an intersection along one line.

4. A C-arm calibration method in accordance with claim 3, wherein said plurality of planes and said normal planes are separated by consecutive angles of 45 degrees.

5. A C-arm calibration method in accordance with claim 1, wherein said plurality of pixels on said image plane comprises at least 4 pixels.

6. A C-arm calibration method in accordance with claim 5, including a step of imaging 2 further voxels outside of said one of said plurality of parallel planes, whereby coordinate information is obtained defining a position for said source in terms of said 2-dimensional mapping.

7. A C-arm calibration method in accordance with claim 6 including a step of deriving values for said transformation parameters from said coordinate information.

8. A C-arm calibration method in accordance with claim 7 including a step of utilizing said 2-dimensional mapping to backproject onto said one of said plurality of said planes an image formed of pixels on said imaging plane.

9. A C-arm calibration method in accordance with claim 8 including a step of utilizing scaling information between planes of said plurality of planes and said 2-dimensional mapping to backproject onto another of said plurality of planes, other than said one, an image formed of pixels on said imaging plane.

* * * * *